(12) United States Patent
Thiel et al.

(10) Patent No.: US 7,202,207 B2
(45) Date of Patent: *Apr. 10, 2007

(54) INDICATIONS OF MANNAN-BINDING LECTIN (MBL) IN THE TREATMENT OF IMMUNOCOMPROMISED INDIVIDUALS

(76) Inventors: Steffen Thiel, Villadsensvej 3, DK-8240 Risskov (DK); Jens Christian Jensenius, Finsens Alle 28, DK-5230 Odense (DK)

( * ) Notice: Subject to any disclaimer, the term of this patent is extended or adjusted under 35 U.S.C. 154(b) by 270 days.

This patent is subject to a terminal disclaimer.

(21) Appl. No.: 10/424,769

(22) Filed: Apr. 29, 2003

(65) Prior Publication Data

US 2003/0191052 A1    Oct. 9, 2003

Related U.S. Application Data

(63) Continuation of application No. 09/568,142, filed on May 10, 2000, now Pat. No. 6,562,784.

(30) Foreign Application Priority Data

May 14, 1999   (DK) ................................. 199900668
Oct. 20, 1999   (DK) ................................. 199901508

(51) Int. Cl.
  *C07K 14/00*    (2006.01)
  *A61K 38/00*    (2006.01)
  *A61K 38/16*    (2006.01)

(52) U.S. Cl. .................... 514/8; 514/2; 514/12; 514/54; 424/9.1; 435/69.1; 435/320.1; 435/252.3; 530/350; 536/23.5

(58) Field of Classification Search .................... 514/2, 514/8, 12, 54; 424/9.1; 435/69.1, 320.1, 435/252.3; 530/350; 536/23.5
See application file for complete search history.

(56) References Cited

U.S. PATENT DOCUMENTS

| 5,112,952 | A | 5/1992 | Mallia et al. |
| 5,270,199 | A | 12/1993 | Ezekowitz |
| 6,562,784 | B1 * | 5/2003 | Thiel et al. ..................... 514/8 |

FOREIGN PATENT DOCUMENTS

| EP | 0856580 | 8/1998 |
| WO | 8901519 | 2/1989 |
| WO | 9910001 | 3/1999 |
| WO | 9964453 | 12/1999 |

OTHER PUBLICATIONS

Yokota, et al., "Oligomeric Structures Required for Complement Activation of Serum Mannan-Binding Proteins," *J. BIOCHEM.* 117:414-419 (1995).
Weis, et al., "The C-type Lectin Superfamily in the Immune System," *Immunological Reviews* 163:19-34 (1998).
Holmskov, et al., "Collectins: Collagenous C-type Lectins of the Innate Immune Defense System," *Immunology Today* 15(2): 67-74 (1994).
Turner, "Mennose-binding Lectin: the Pluripotent Molecule of the Innate Immune System," *Immunology Today* 17(11):532-540 (1996).
Janeway, et al., "Immunobiology, The Immune System in Health and Disease," Fourth Edition, Churchill Livingston (1999), Title only.
Matsushita, et al., "Activation of the Classical Complement Pathway by Mannose-binding Protein in Association with a Novel C1s-like Serine Protease," *J. Exp. Med.* 176:1497-1502 (1992).
Thiel, et al., "A Second Serine Protease Associated with Mannan-binding Lectin that Activates Complement," *NATURE* 386:506-510 (1997).
Stover, et al., "Two Constituents of the Initiation Complex of the Mannan-Binding Lectin Activation Pathway of Complement are Encoded by a Single Structural Gene," *The Journal of Immunology* 162:3481-3490 (1999).
Holmskov, et al., "The Concentration of the C-type Lectin, Mannan-binding Protein, in Human Plasma Increases During an Acute Phase Response," *Clin. Exp. Immunol.* 90:31-35 (1992).
Madsen, et al., "A New Frequent Allele is the Missing Link in the Structural Polymorphism of the Human Mannan-binding Protein," *IMMUNOGENETICS* 40:37-44 (1994).
Summerfield, et al., "Mannose Binding Protein Gene Mutations Associated with Unusual and Severe Infections in Adults," *The Lancet* 345:886-889 (1995).
Garred, et al., "Increased Frequency of Homozygosity of Abnormal Mannan-binding-protein-Alleles in Patients with Suspected Immunodeficiency," *The Lancet* 346:941-943 (1995).
Summerfield, et al., "Association of Mutations in Mannose Binding Protein Gene with Childhood Infection in Consecutive Hospital Series," *BMJ* 314:1229-1232 (1997).
Emmerik, et al., "Binding of Mannan-Binding Protein to Various Bacterial Pathogens of Meningitis," *Clin. Exp. Immunol.* 97:411-416 (1994).

(Continued)

*Primary Examiner*—Chih-Min Kam
(74) *Attorney, Agent, or Firm*—Iver P. Cooper

(57) ABSTRACT

The present invention relates to the use of a composition comprising at least one mannan-binding lectin (MBL) subunit, or at least one mannan-binding lectin (MBL) oligomer comprising the at least one mannan-binding lectin (MBL) subunit, in the manufacture of a medicament for prophylaxis and/or treatment of infection. In particular the invention relates to prophylaxis and/or treatment of infection in an individual having an immunocompromised condition; and/or an individual being at risk of acquiring an immunocompromised condition resulting from a medical treatment. The present invention is particular relevant for prophylaxis and/or treatment of infection in individuals suffering from neutropenia, in particular as prophylaxis and/or treatment of infection in individuals receiving or going to receive chemotherapy or similar treatment. The individuals may be treated independent on their serum MBL level, and it has been shown that in particular individuals having a serum MBL level in the range of from 50 ng/ml serum to 500 ng/ml serum may benefit from the prophylaxis and/or treatment.

43 Claims, 2 Drawing Sheets

OTHER PUBLICATIONS

Figure 1:
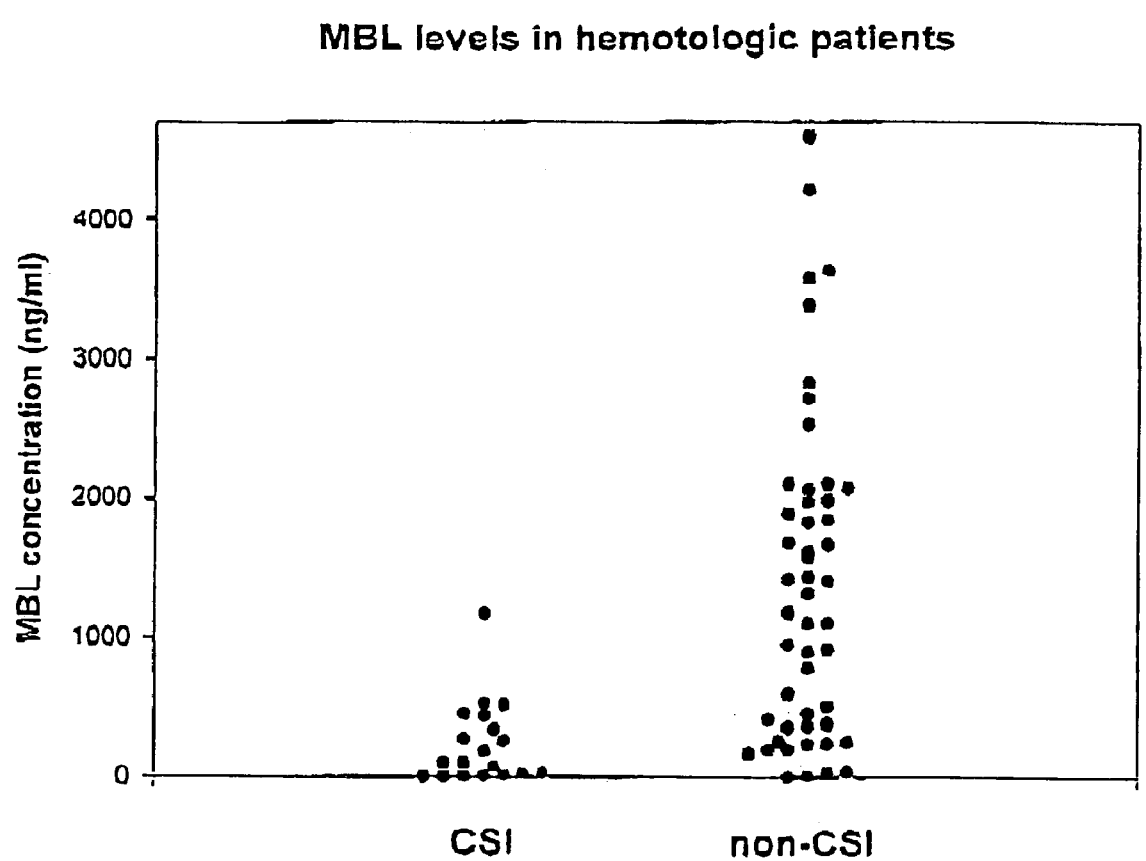

Jack, et al., "Activation of Complement by Mannose-Binding Lectin on Isogenic Mutants of *Neisseria meningitidis* Serogroup B," *The Journal of Immunology* 160:1346-1353 (1998).

Miller, et al., "A Familial, Plasma-associated Defect of Phagocytosis," *The Lancet* pp. 60-63 (1968).

Super, et al., "Association of Low Levels of Mannan-binding Protein with a Common Defect of Opsonisation," *The Lancet* 2:1236-1239 (1989).

Nielsen, et al., "The Level of the Serum Opsonin, Mannan-binding Protein in HIV-1 Antibody-Positive Patients," *Clin. Exp. Immunol.* 100:219-222 (1995).

Christiansen, et al., "Mannan-binding Lectin Deficiency is Associated with Unexplained Recurrent Miscarriage," *Scand. J. Immunol.* 49:193-196 (1999).

Garred, et al., "Dual Role of Mannan-binding Protein in Infections: Another Case of Heterosis?," *European Journal of Immunogenetics* 21:125-131 (1994).

Hoal-van Helden, et al., "Mannose-Binding Protein B Allele Confers Protection Against Tuberculous Meningitis," *Pediatric Research* 45(4):459-464 (1999).

Fischer, et al., "Mannan-Binding Protein and Bovine Conglutinin Mediate Enhancement of Herpes Simplex Virus Type 2 Infection in Mice," *Scand. J. Immunol.* 39:439-445 (1994).

Valdimarsson, et al., "Reconstruction of Opsonizing Activity by Infusion of Mannan-Binding Lectin (MBL) to MBL-Deficient Humans," *Scand. J. Immunol.* 48:116-123 (1998).

Pizzo, "Drug Therapy: Management of Fever in Patients with Cancer and Treatment-Induced Neutropenia," *The New England Journal of Medicine* 328(18):1323-1332 (1993).

Aittoniemi, et al., "Opsonising Immunoglobulins and Mannan-Binding Lectin in Chronic Lymphocytic Leukemia," *Leukemia and Lymphoma* 34(3-4):381-385 (1999).

Lehrnbecher, et al., "Assessment of Measuring Circulating Levels of Interleukin-6, Interleukin-8, C-Reactive Protein, Soluble Fc$\gamma$ Receptor Type III, and Mannose-Binding Protein in Febrile Children with Cancer and Neutropenia," *Clinical Infectious Diseases* 29:414-419 (1999).

Lu, et al., "Binding of the Pentamer/Hexamer Forms of Mannan-Binding Protein to Zymosan Activities the Proenzyme $CIr_2CIS_2$ Complex, of the Classical Pathway of Complement, without Involvement of CIq," *The Journal of Immunology* 144:2287-2294 (1990).

Sastry, et al., "Exon Structure Reveals its Evolutionary Relationship to a Human Pulmonary Surfactant Gene and Localization to Chromosome 10," *J. Exp. Med.* 170:1175-1189 (1989(.

Lipscombe, et al., "Distinct Physicochemical Characteristics of Human Mannose Binding Protein Expressed by Individuals of Differing Genotype," *Immunology* 85:660-667 (1995).

Makrides, "Components of Vectors for Gene Transfer and Expression in Mammalian Cells," *Protein Expression and Purification* 17:183-202 (1999).

* cited by examiner

INDICATIONS OF MANNAN-BINDING LECTIN (MBL) IN THE TREATMENT OF IMMUNOCOMPROMISED INDIVIDUALS

The present application is a continuation of U.S. Ser. No. 09/568,142 filed May 10, 2000, now U.S. Pat. No. 6,562,784, which claims foreign priority benefits of Denmark Application No. 199900668, filed May 14, 1999 and Denmark Application No. 199901508, filed Oct. 20, 1999.

TECHNICAL FIELD

The present invention pertains to the use of subunits and oligomers of mannan-binding lectin (MBL) in prophylactic and/or curative treatment of an immunocompromised individual.

BACKGROUND OF THE INVENTION

Several groups of lectins, i.e., carbohydrate-binding proteins, are known in man. One group is the C-type lectins. The C-type lectins contain a calcium-dependent carbohydrate recognition domain (a C-type CRD)[1]. Mannan-binding lectin (MBL), synonymous to mannose-binding lectin, mannan-binding protein or mannose-binding protein (MBP), belongs to the subgroup of C-type lectins, termed collectins, since these soluble proteins are composed of subunits presenting three CRDs attached to a collagenous stalk[2]. MBL interact with carbohydrates presented by a wide range of micro-organisms and accumulating evidence shows that it plays an important role in the innate immune defence[3]. When bound to carbohydrate MBL is able to activate the complement system.

The complement system may be activated via three different pathways: the classical pathway, the alternative pathway, and the newly described third pathway, the mannan-binding lectin (MBL) pathway which is initiated by the binding of MBL to carbohydrates presented by microorganisms. The components of the alternative pathway and of the MBL pathway are parts of the innate immune defence, also termed the natural or the non-clonal, immune defence, while the classical pathway involves cooperation with antibodies of the specific immune defence[4].

The human MBL protein is composed of up to 18 identical 32 kDa polypeptide chains[27], each comprising a short N-terminal segment of 21 amino acids including three cysteine residues, followed by 7 repeats of the collagenous motif Gly-X-Y interrupted by a Gln residues followed by another 12 Gly-X-Y repeats. A small 34 residue 'neck-region' joins the C-terminal $Ca^{2+}$-dependent lectin domain of 93 amino acids with the collagenous part of the molecule[28].

The collagenous regions of the three polypeptide chains combine to form a subunit which is stabilised covalently by disulphide bridges. Individual subunits are joined by disulphide bridges as well as by non-covalently interactions[27].

The position of these disulphide bridges has, however, not been fully resolved. SDS-PAGE analysis under non-reducing conditions of MBL shows bands with an apparent molecular weight (m.w.) larger than 200 kDa presumably representing blocks of 3, 4, 5 and even 6 assembled subunits[27].

The actual number of subunits in the natural human MBL protein has been controversial. Lipscombe et al. (1995) obtained data by use of ultracentrifugation suggesting 25% of human serum MBL to be made of 2–3 subunits and only a minor fraction reaching the size of 6 subunits. The relative quantification was carried out by densitometry of Western blots developed by chemiluminescence[27] found by SDS-PAGE analysis of fractions from ion exchange chromatography that the predominant species of covalently linked MBL subunit chains consisted of tetramers while only pentameric or hexameric complexes activated complement. Gel permeation chromatography (GPC) analysis, in contrast, suggests that MBL is comparable in size with the C1 complex. GPC can be carried out under conditions which allow for a study of the importance of weak protein-protein interactions in the formation of MBL molecules. MBL content in the GPC fractions can be determined by standard MBL assay techniques.

MBL is synthesized in the liver by hepatocytes and secreted into the blood. It binds to carbohydrate structures on bacteria, yeast, parasitic protozoa and viruses, and exhibits antibacterial activity through killing of the microorganisms by activation of the terminal, lytic complement components or through promotion of phagocytosis (opsonization). The sertiform structure of MBL is quite similar to the bouquet-like structure of C1q, the immunoglobulin-binding subcomponent of the first component in the classical pathway[3]. C1q is associated with two serine proteases, C1r and C1s, to form the C1 complex. Similarly, MBL is associated with two serine proteases MASP-1[5] and MASP-2[6], and an additional protein called Map19[7]. MASP-1 and MASP-2 have modular structures identical to those of C1r and C1s[6]. The binding of MBL to carbohydrates induces the activation of MASP-1 and MASP-2. MASP-2 then generates the C3 convertase, C4bC2b, through cleavage of C4 and C2. Reports suggest that MASP-1 may activate C3 directly. Nothing is known about the stoichiometry and activation sequence of the MBL/MASP complexes. MBL has also been characterized in other animals such as rodents, cattle, chicken and monkeys.

The concentration of MBL in human serum is largely genetically determined, but reportedly increases up to threefold during acute phase reactions[8]. Three mutations causing structural alterations and two mutations in the promotor region are associated with MBL deficiency[9]. MBL deficiency is associated with susceptibility to a variety of infections. Examination of five adult individuals with unusual and severe infections showed three to be homozygous for structural MBL mutations and two to be heterozygous[10]. Investigation of 229 children referred to the Danish National Hospital because of non-HIV-related immunodeficiency showed a tenfold higher frequency of homozygosity for structural MBL mutant alleles than seen in a control group[11]. Allotyping of 617 consecutively hospitalized children at St Mary's Hospital in London showed significantly higher frequency of homozygosity and heterozygosity for mutant allotypes in the infected children than in the noninfected[12].

A wide range of oligosaccharides can bind to MBL. As the target sugars are not normally exposed on mammalian cell surfaces at high densities, MBL does not usually recognize self-determinants, but is particularly well suited to interactions with microbial cell surfaces presenting repetitive carbohydrate determinants. In vitro, yeast (*Candida albicans* and *Cryptococcus neoformans*), viruses (HIV-1, HIV-2, HSV-2, and various types of influenza A) and a number of bacteria have been shown to be recognized by MBL. In the case of some bacteria, the binding with MBL is impaired by the presence of a capsule[13]. However, even encapsulated bacteria (*Neisseria meningitidis*) can show strong binding of MBL[14].

The microorganisms, which infect MBL deficient individuals, represent many different species of bacterial, viral and fungal origin[12,15-17]. Deficiency is also associated with habitual abortions[18]. Indeed, MBL could be a general defence molecule against most bacteria, and thus be considered as one reason why so many bacteria are non-pathogenic.

While accumulating data support the notion of a protective effect of MBL there are also observations suggesting that infections with some microorganisms, notably intracellular pathogens, attain a higher frequency in MBL sufficient than in MBL deficient individuals[19,20]. This is in concordance with the results of an animal experiment, where an increased number of HSV-2 were found in the liver of mice pre injected with human MBL[21].

Clinical grade MBL has been obtained from blood donor plasma and shown to be safe upon infusion[22]. Production of recombinant MBL conceivably having a structure and an activity similar to that of native MBL has been attained (patent application PA 1999 00668/C5/KH).

SUMMARY OF THE INVENTION

The invention features the use of MBL, purified from natural sources or from material produced by recombinant technologies, or by any other suitable MBL-producing cell line, for the prophylaxis and/or treatment of infections. The condition may be associated with a therapeutical or medical treatment, such as e.g. the use of cytotoxic therapy. The MBL may be given before or after start of the medical treatment and for any duration of time deemed suitable.

The invention also relates to treating individuals having normal MBL levels, as such individuals are likely to benefit—prior to any cell toxic treatment—from MBL administration.

Accordingly, the invention in one aspect relates to treatment and/or prophylaxis of infections in individuals suffering from an immunocompromised condition, or to treatment of individuals who are likely to contract such a condition due to treatment known to be associated with the occurence of an immunocompromised condition. Examples of such treatments are e.g. chemotherapy and radiation therapy such as e.g. x-ray treatment.

Chemotherapy and radiation therapy are offered as part of the treatment of several forms of cancers, aiming either at slowing the progression of the disease or reversing said progression by means of a curative treatment. Chemotherapy and radiation therapy are immunocompromising since cells of the immune system are being killed, thus leading to a state of immunosuppression especially characterized by neutropenia.

MBL is believed to exert its antimicrobial activity mainly through its opsonizing activity (preparation of microorganisms for phagocytosis). This activity is dependent on activation of complement after binding of MBL to the microbial surface and deposition of C4b and C3b on the microorganism. MBL can also promote the direct complement-mediated killing of the microorganism through the activation of the terminal lytic pathway of complement and insertion of the membrane attack complex (MAC) in the membrane. This mechanism is considered of minor importance. Many microorganisms, such as Gram-positive bacteria, e.g., Streptococcus pneumonia, are resistant to MAC, but can be eliminated by opsonophagocytosis. Considering opsonophagocytosis as the main effector mechanism of MBL-mediated clearance of microorganisms, it is a surprise that MBL treatment could be of benefit to persons being deficient of the most important phagocytic cells, i.e., the neutrophiles.

The importance of neutropenia in the risk of serious infections in individuals with cancer who are receiving cytotoxic chemotherapy was recognized nearly 30 years ago[23]. Infections thus occur very frequent in haematological and other cancer individuals undergoing chemotherapy and other immunocompromising therapeutic interventions. Synchronous with the intensified use of chemotherapy, problems with infections are increasing and are now a major challenge in supportive care[24]. Accordingly, all haematology and oncology departments use many resources on fighting infections. This fight is steadily getting more difficult due to the appearance of multi resistant bacterial strains.

Individuals being devoid of the important cellular components of the immune system during or after an immunocompromising condition are dependent on an efficient innate humoral immune system, such as the complement system, e.g. during periods of neutropenia. No sufficiently accurate and reliable prognostic factors are presently capable of predicting an increased risk of serious infections in individuals treated with chemotherapy, radiation therapy, or other immunocompromising treatments[24].

Accordingly, an immunocompromising condition arising from a medical treatment is likely to expose the individual in question to a higher risk of infection. It is possible according to the invention to prophylactically treat an infection in an individual having the immunocompromised condition before or during treatments known to generate such a condition. By prophylactically treating with MBL before or during a treatment known to generate such a condition it is possible to prevent a subsequent infection or to reduce the risk of the individual contracting an infection due to the immuno-compromised condition. Should the individual contract an infection e.g. following a treatment leading to an immunocompromised condition it is also possible to treat the infection by administering to the individual an MBL composition according to the invention.

The invention is also directed to treatments of such deficiencies by infusion of MBL. Furthermore, the invention is directed to the use of MBL plasma concentrations for predicting the risk of infection of individuals undergoing e.g. chemotherapy.

In another aspect the present invention is related to the use of a composition comprising at least one mannan-binding lectin (MBL) subunit, or at least one oligomer comprising the at least one mannan-binding lectin (MBL) subunit, in the manufacture of a medicament for prophylactic, ameliating or curative treatment of an infection in an individual initially having plasma levels of MBL in excess of 50 ng/ml. In particular the individual may be genetically disposed to an MBL deficiency or have acquired an MBL deficiency leading to an increased risk of suffering from infections. Accordingly, the invention also concerns treatment of infections in individuals suffering from a mannan-binding lectin (MBL) deficiency including any deficiency in the production of MBL and/or function of MBL.

In yet another aspect there is provided a method for estimating the probability of the occurrence of any clinically significant infection in an individual undergoing chemotherapy or any other form of immunocompromising treatment, said method comprising the step of measuring the concentration of MBL in plasma or serum obtained from the individual, and estimating the probability on the basis of the measured concentration.

In the present context immunocompromised is used in its normal meaning, i.e. an individual not being capable of evoking an adequate immune response due to primary or secondary deficiency, induced or non-induced, in one or more of the elements of the normal immune defence system.

DETAILED DESCRIPTION OF THE INVENTION

Until now MBL has been used for treating MBL deficiency as such which has been defined by an arbitrary level of below 50 ng/ml, or more often below 10 ng/ml serum which is often identical with the sensitivity of various MBL test assays, and the level has therefore been set as the level for which substantially no MBL could be detected in the various prior art assays.

By the present invention it has been shown that infections may be prevented and/or treated in immunocompromised individuals independent on their serum MBL level. In particular infections may be prevented in immunocompromised individuals when administering MBL to these individuals having an MBL level in excess of 50 ng/ml serum. Also, individuals having an MBL level in excess of 75 ng/ml serum may be in need of treatment, such as individuals having an MBL level in excess of 100 ng/ml serum, and individuals having an MBL level in excess of 150 ng/ml serum.

Also the MBL treatment of infections may be conducted by administering MBL to these individuals in combination with relevant antibiotics, anti-viral agents or anti-fungal agents.

In particular, individuals at risk of acquiring an immuno-compromised condition resulting from a medical treatment will benefit from being prophylactically treated with MBL before, during and maybe also after the treatment in order to prevent diseases associated with the immuno-compromised condition, such as infections.

Generally all individuals being immuno-compromised or at risk of becoming immuno-compromised should be treated with MBL independent on their specific MBL level. The reason behind this is that infection may lead to MBL depletion, and therefore an MBL "booster", increasing the MBL level initially will reduce the risk of MBL depletion to a level below a deficiency level, and the immune defence of these patients can be reinforced by administration of recombinant or natural plasma-derived MBL. In particular infections may be prevented when administering MBL to individuals having an MBL level in excess of 50 ng/ml serum. Also, individuals having an MBL level in excess of 75 ng/ml serum may be in need of treatment, such as individuals having an MBL level in excess of 100 ng/ml serum, and individuals having an MBL level in excess of 150 ng/ml serum.

The present inventors have also shown herein that in particular individuals having an MBL level below 500 ng/ml serum will benefit from MBL treatment in relation to an immuno-compromised condition. Consequently, in particular individuals having an MBL level below 400 ng/ml will benefit, such as individuals having an MBL level below 300 ng/ml, such as individuals having an MBL level below 250 ng/ml, such as individuals having an MBL level below 200 ng/ml.

Thus, in a preferred embodiment the present invention relates to the use of MBL for manufacturing of a medicament for of individuals having an MBL level in serum in the range of 50–500 ng/ml, such as in the range of 100–500 ng/ml for treating and/or preventing infections, in particular in relation to an immunocompromised condition of the individual.

The immuno-compromised condition may be due to a medical treatment as discussed above, i.e. chemotherapy or other immuno-suppressing treatment, such as induced by treatment with steroids, cyclophosphamide, azathioprine, metotrexate, cyclosporine, and/or rapamycin, in particular in relation to cancer treatment.

Also, the immuno-compromised condition may be due to an acquired immunodeficiency, such as AIDS, or leucemia, in particular neutropenia or other secondary immuno-deficiencies.

Furthermore, individuals having an MBL level above 50 ng/ml and below 500 ng/ml will benefit from MBL treatment in general, in order to prevent infections, in particular chronic infections.

One group of individuals being in need of MBL treatment in order to prevent and/or treat infections are individuals having a low level of functional MBL, independent on the level of MBL as such. This is due to the fact, that for some mutations of the MBL it has been found, that although MBL subunits and oligomers thereof are expressed in serum the functionality thereof are low. The functionality or functional activity of MBL may be estimated by its capacity to form an MBL/MASP complex leading to activation of the complement system. When C4 is cleaved by MBL/MASP an active thiol-ester is exposed and C4 becomes covalently attached to nearby nucleophilic groups. A substantial part of the C4b will thus become attached to the coated plastic well and may be detected by anti-C4 antibody.

A quantitative TRIFMA for MBL functional activity is constructed by 1) coating microtitre wells with 1 mg mannan in 100 ml buffer; 2) blocking with Tween-20; 3) applying test samples, e.g. diluted MBL preparations 4) applying MBL deficient serum (this leads to the formation of the MBL/MASP complex); alternatively the MBL and the MBL deficient serum may be mixed before application with the microtitre wells; 5) applying purified complement factor C4 at 5 mg/ml; 6) incubate for one hour at 37° C.; 7) applying Eu-labelled anti-C4 antibody; 8) applying enhancement solution; and 9) reading the Eu by time resolved fluorometry. Between each step the plate is incubated at room temperature and washed, except between step 8 and 9.

Estimation by ELISA may be carried out similarly, e.g. by applying biotin-labelled anti-C4 in step 7; 8) apply alkaline phosphatase-labelled avidin; 9) apply substrate; and 10) read the colour intensity.

The functionality may be expressed as the specific activity of MBL, such as 1 unit of MBL activity per ng MBL. A non-functional MBL may be defined as MBL having a specific activity less than 50% of plasma MBL specific activity, such as less than 25% of plasma MBL specific activity, wherein the plasma MBL is purified from an individual not suffering from any MBL mutations. In particular the reference plasma MBL is plasma pool LJ 6.57 Apr. 28, 1997.

Thus, the present invention also relates to the prevention and/or treatment of infection in individuals having a mutation in their MBL gene leading to a reduced expression of MBL and/or expression of non-functional MBL.

In particular such mutations in the MBL gene can lead to a change of aminoacid number 52 (numbering including the leader peptide of MBL) from arginine to cysteine, aminoacid number 54 from glycine to aspartic acid or amino acid number 75 from glycine to glutamic acid.

Also mutations in the promoter region of the MBL gene can lead to lowered levels of MBL. In particular mutations at position—and at position—221 have an influence on the expression of MBL.

The MBL sequence may be found in swiss.prot under accession No: 11226

The MBL composition used to manufacture an MBL medicament may be produced from any MBL source available. The MBL source may be natural MBL, whereby the MBLs are produced in a native host organism, meaning that MBL is produced by a cell normally expressing MBL. One usual method of producing an MBL composition is by extraction of MBL from human body liquids, such as serum or plasma, but MBL may also be harvested from cultures of hepatocytes.

In another aspect the MBL oligomers are produced by a host organism not natively expressing an MBL polypeptide, such as by recombinant technology.

In a first embodiment the MBL source may be serum, from which an MBL composition is obtained by purification from serum, plasma, milk product, colostrum or the like by a suitable purification method, such as affinity chromatography using carbohydrate-derivatised matrices, such as mannose or mannan coupled matrices. Such a method is discussed in WO99/64453, wherein the purification process is followed by a virus-removal step in order to remove infectious agents from the MBL source, since one of the major problems with proteins purified from body liquids is the risk of introducing infectious agents in combination with the desired protein. WO99/64453 is hereby incorporated by reference.

The MBL composition used to manufacture an MBL medicament preferably comprises MBL oligomers having a size distribution substantially identical to the size distribution of MBL in serum, such as a size distribution profile at least 50% identical to the size distribution profile of MBL in serum. By identical is meant that at least 50% of the oligomers has an apparent molecular weight higher than 200 kDa, when analysed by SDS-PAGE and/or Western blot.

In a more preferred embodiment the size distribution profile is at least 75% identical to the size distribution profile of MBL in serum, such as at least 90% identical to the size distribution profile of MBL in serum, and more preferred at least 95% identical to the size distribution profile of MBL in serum.

When purifying from an MBL source initially having another size distribution profile it is preferred that the affinity chromatography used to purify from the MBL source favours purification of oligomers having an apparent molecular weight higher than 200 kDa. This is obtained by using a carbohydrate-derivatized matrix having substantially no affinity to subunits and/or dimers of MBL. Preferably the carbohydrate-derivatized matrix has affinity for substantially only tetrameric, pentameric and/or hexameric recombinant MBLs.

The matrix may be derivatized with any carbohydrate or carbohydrate mixture whereto MBL binds and for which binding of the higher oligomers of MBL are favoured. The carbohydrate-cerivatized matrix is preferably a hexose-derivatized matrix, such as a mannose- or a N-acetyl-glucosamin derivatized matrix, such as most preferably a mannose-derivatized matrix.

The selectivity of the carbohydrate-derivatized matrix is obtained by securing that the matrix as such, i.e the un-derivatized matrix has substantially no affinity to MBL polypeptides, in particular no affinity to MBL trimers or smaller oligomers. This may be ensured when the matrix as such is carbohydrate-free. In particular the matrix should not contain any Sepharose or the like. It is preferred that the matrix consists of a non-carbohydrate containing polymer material, such as Fractogel®TSK beads The matrix may be in any form suitable for the chromatography, mostly in the form of beads, such as plastic beads.

After application of the MBL source the column is washed, preferably by using non-denaturing buffers, having a composition, pH and ionic strength resulting in elimination of proteins, without eluting the higher oligomers of MBL. Such as buffer may be TBS. Elution of MBL is performed with a selective desorbing agent, capable of efficient elution of highed oligomers of MBL, such as TBS comprising a desorbing agent, such as EDTA (for example 5 mM EDTA) or mannose (for example 50 mM mannose), and MBL oligomers are collected. Such a purification method is described in co-pending International patent application having the title "Recombinant Human Mannan Binding Lectin" filed the same day as the present application.

In a preferred aspect a clinical grade MBL composition is obtained by using an MBL source produced by recombinant technology, wherein the MBL source is the culture media from culturing of MBL producing cells.

Thus, the present invention encompasses MBL produced by a process of producing a recombinant mannan binding lectin (MBL), comprising the steps of:
preparing a gene expression construct comprising a DNA sequence encoding a MBL polypeptide or a functional equivalent thereof,
transforming a host cell culture with the construct,
cultivating the host cell culture, thereby obtaining expression and secretion of the polypeptide into the culture medium, followed by
obtaining a culture medium comprising human recombinant MBLs.

The culture medium comprising the human recombinant MBL polypeptides may then be processed as described above for purification of MBL.

The MBL polypeptide is preferably a mammalian MBL polypeptide, such as more preferably a human MBL polypeptide. The gene expression construct may be produced by conventional methods known to the skilled person, such as described in U.S. Pat. No. 5,270,199.

In another embodiment the gene expression construct is prepared as described in Danish Patent application No: PA 1999 00668 or in co-pending International patent application having the title "Recombinant Human Mannan Binding Lectin" filed the same day as the present application.

The expression is preferably carried out in e.g. mammalian cells, the preparation according to the invention results from the use of an expression vector comprising intron sequence(s) from an MBL gene and at least one exon sequence. Regarding the transgenic animals as expression system this term is in this context animals which have been genetically modified to contain and express the human MBL gene or fragments or mimics hereof.

In addition to the purification method it is preferred that the gene expression construct and the host cell also favours production of higher oligomers, which has been found to be possible by using a gene expression construct comprising at least one intron sequence from the human MBL gene or a functional equivalent thereof. malian cells and cells from insects.

In particular the MBL composition is used for treatment and/or prophylaxis of an infection associated with an immunocompromised condition in an individual. Any microbiol infections may be treated and/or prevented with MBL, i.e. any infection caused by a microbial species.

Consequently, the MBL composition may be used for preventing and/or treating an infection in a immuno-compromised individual wherein the microbial species is a fungus, a yeast, a protozoa and/or a bacteria.

Also, the MBL composition may be used for treating infection, wherein the microbial species is resistent to usual medicaments, such as infections for which the bacterial species is resistent to at least one antibiotic medicament. More important is the prophylaxis and/or treatment of infections for which the bacterial species is multiresistent.

The immuno-compromised individuals may suffer from infections caused by pathogenic bacterial species, such as *Streptococcus pneumonia, Salmonella* and *Staphylococcal* species.

It is however well-known that in particular immuno-compromised individuals also often suffer from infections caused by bacterial species, that are normally non-pathogenic, i.e. opportunistic pathogens, e.g. *E. coli* species, and many of these species are resistent to usual antibiotic treatment.

The infection associated with the immuno-compromised condition may also be a viral infection, such as a viral infection wherein the virus is a retrovirus.

Also, the immuno-compromised condition may be an infection with the retrovirus Human Immunodeficiency Virus (HIV). However, the viral infections treated and/or prevented according to the invention are normally not caused by a retrovirus, but may for example be caused by a DNA virus.

The medicament may be produced by using the eluant obtained from the affinity chromatography as such. It is however preferred that the eluant is subjected to further purification steps before being used.

In addition to the MBL oligomers, the medicament may comprise a pharmaceutically acceptable carrier substance and/or vehicles. In particular, a stabilising agent may be added to stabilise the MBL proteins. The stabilising agent may be a sugar alcohol, saccharides, proteins and/or aminoacids. Examples of stabilising agents may be maltose or albumin.

Other conventional additives may be added to the medicament depending on administration form for example. In one embodiment the medicament is in a form suitable for injections. Conventional carrier substances, such as isotonic saline, may be used.

In another embodiment the medicament is in a form suitable for pulmonal administration, such as in the form of a powder for inhalation or creme or fluid for topical application.

The route of administration may be any suitable route, such as intravenously, intramusculary, subcutanously or intradermally. Also, pulmonal or topical administration is envisaged by the present invention.

The MBL composition may also be administered simultaneously, sequentially or separately with another treatment, said other treatment resulting in an immunocomprosmising condition in the individual, such as chemotherapy. The medicament may be administered for a period before the onset of administration of chemotherapy or the like and during at least a part of the chemotherapy.

The MBL composition is administered in suitable dosage regimes, in particularly it is administered repeatedly at suitable intervals, such as once or twice a week, starting before onset of chemotherapy and maintained at intervals, for example once a week, at least during a part of the chemotherapy period, preferably during the whole chemotherapy period.

Normally from 1–100 mg is administered per dosage, such as from 2–10 mg, mostly from 5–10 mg per dosage depending on the individual to be treated, for example about 0.1 mg/kg body weight is administered.

The use of an MBL composition may also be in a kit-of-parts further comprising another medicament, such as an anti-fungal, anti-yeast, anti-bacterial and/or anti-viral medicament.

The anti-viral medicament may be a medicament capable of virus attenuation and/or elimination.

The invention also relates to an aspect of using a measurement of the MBL level as a prognostic marker for the risk of the individual of acquiring an infection, and thereby an indicative of the need for treatment. In particular an MBL level below 500 ng/ml is a prognostic marker indicative for treatment with MBL, in particular in relation to an immuno-compromised individual or an individual at risk of being immuno-compromised.

The prognostic marker may be in relation to any infection, but is especially relevant as a prognostic marker for septicaemia or pneumonia in individuals undergoing immuno-compromising cell toxic therapy.

Thus, the present invention also relates to a method of using an MBL composition for preventing and/or reducing infections in an individual, the method comprising the steps of:

i) determining serum levels of MBL in an individual,
ii) estimating the probability of the occurence of a significant clinical infection in the individual, and optionally, administering an MBL composition to the individual.

The MBL level is measured in serum or plasma, and may be determined by time resolved immunofluorescent assay (TRIFMA), ELISA, RIA or nephelometry.

Also the MBL levels may be inferred from analysis of genotypes of the MBL genes as discussed above in relation to mutations of MBL leading to a decreased MBL level.

The invention has now been explained and accounted for in various aspects and in adequate details, but additionally it will be illustrated below by FIGS. 1 and 2 and the non-limiting examples of preferred embodiments.

FIGURE LEGENDS

FIG. 1: The distribution of MBL concentrations in the plasma of in leukemia patients divided into patients with clinically significant infections (CSI) and non-CSI patients.

Figure 2:
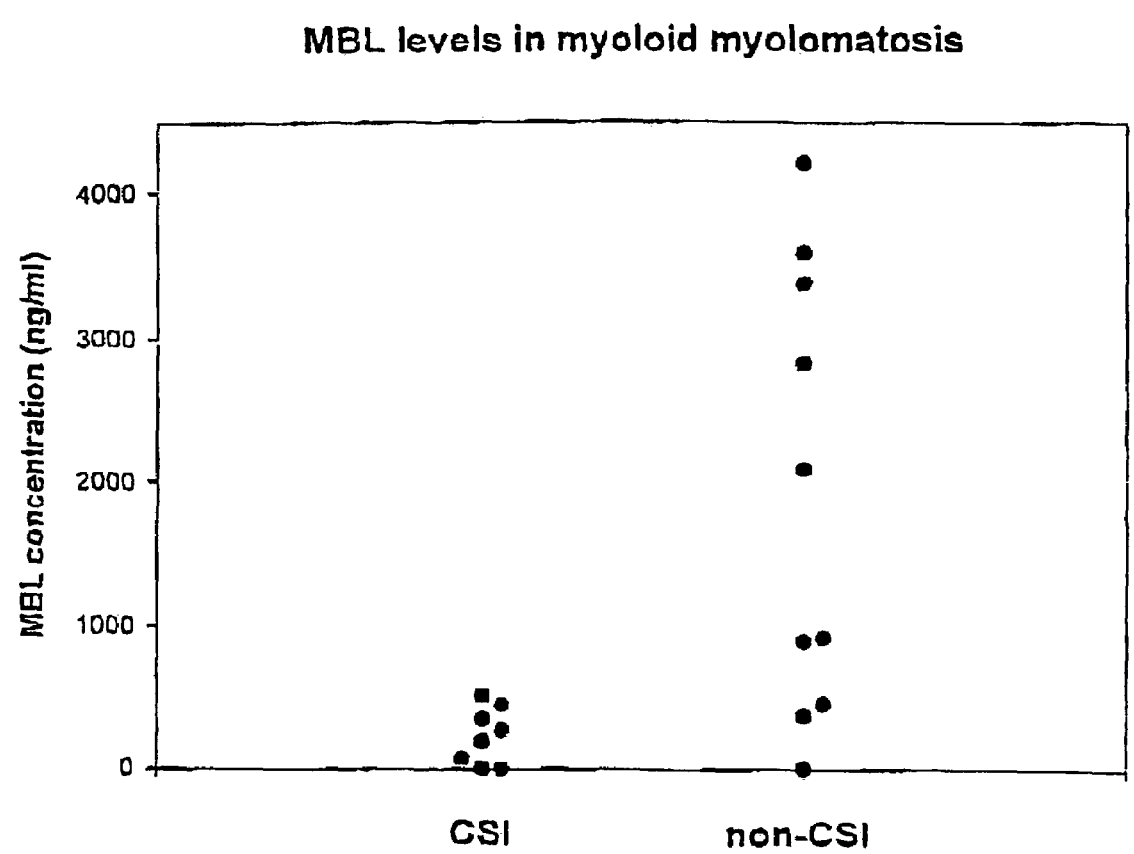

FIG. 2: The distribution of MBL concentrations in the plasma of multiple myeloma patients divided into those with clinically significant infections (CSI) and non-CSI patients.

EXAMPLE

The following example demonstrates the results of an examination of the influence of MBL deficiency on the occurrence of clinically significant infections in a group of hematologic individuals undergoing chemotherapy.

Study Population

The study encompasses examination of a consecutive series of patients attending Department of Haematology, Aarhus University, Denmark. The majority of these patients received chemotherapy. They included 7 with acute myeloid leukaemia, 17 with multiple myeloma (MM), 11 with polycytemia, 13 with Non-Hodgkin's lymphoma, 1 with Burkitt's lymphoma, 1 with Waldenström's macroglobulinemia, 5 with chronic lymphocytic leukaemia, 3 with monoclonal gammapathy of undetermined significance (MGUS), 5 with Hodgkin's lymphoma, 2 with chronic myeloid leukaemia, 1 with acute lymphoid leukaemia, 1 with aplastic anaemia and 1 with myelofibrosis. With regard to the MM group they all received chemotherapy. Three different treatments were used; VAD: vincristine (0.4 mg per 24 hours) and doxorubicin (Adriamycin) (9 mg per m$^2$ per 24 hours) given by continuous infusion for 4 days and dexamethasone (40 mg, p.o.) for 4 days on days 1 through 4, 9 through 12 and 17 through 20 of each 28 day cycle; NOP: mitoxantron (10 mg per m$^2$) and vincristine (1,4 mg per m$^2$) given by continuous infusion one time and prednisone (2×50 mg, p.o.) every day of each cycle; MP: melphalan (0.25 mg/kg/day) by infusion for 4 days and prednisone (2×50 mg, p.o.) for 4 days.

Patients presenting clinically significant infections (CSI, defined as bacteriaemia or pneumonia) were identified by retrospective computer search of the patient database. Of the MM patients with CSI, 4 had pneumococcal pneumonia, 3 had non specified pneumonia, 1 had pneumonia due to *Staphylococcus aureus*.

Before entering chemotherapy blood was drawn into evacuated glass tubes containing EDTA (final concentration about 10 mM). The plasma was aliquoted and kept at −80° C. until assay. Plasma samples were similarly obtained from healthy blood donors. The patients were free of infections at the time of blood sampling.

Assay for MBL

The concentration of MBL were determined by a time resolved immunofluorescent assay (TRIFMA). Microtitre wells (fluoroNunc, Nunc, Kamstrup, Denmark) were coated with antibody by incubation overnight at room temperature with 500 ng anti-human MBL antibody (Mab 131–1, Statens Serum Institut, Copenhagen, Denmark) in 100 µl PBS (0.14 M NaCl, 10 mM phosphate, pH 7.4). After wash with Tween-containing buffer (TBS, 0.14 M NaCl, 10 mM Tris/HCl, 7.5 mM NaN$_3$, pH 7.4 with 0.05% Tween 20) test samples (plasma 1/20) and calibrator dilutions were added in TBS/Tween with extra NaCl to 0.5 M and 10 mM EDTA.

After overnight incubation at 4° C. and wash, the developing europium-labelled antibody (12.5 ng Mab 131-1 labelled with the Eu-containing chelate, isothiocyanato-benzoyl-diethylene-triamine-tetra acetic acid, according to the manufacturer, Wallac, Turku, Finland) was added in TBS/Tween with 25 µM EDTA.

Following incubation for 2 h and wash, fluorescence enhancement solution was added (Wallac) and the plates were read on a time resolved fluorometre (Delfia 1232, Wallac). The calibration curve was made using dilutions of one plasma, which was kept alliquoted at −80° C. The concentration of MBL in this plasma (3.6 µg/ml) was determined by comparison with highly purified MBL, which was quantified by quantitative amino acid analysis.

Results

No difference in the number of MBL deficient individuals can be found between haematological patients and normal persons.

A significant lower level of MBL was observed in hematologic patients with CSI as compared to non-CSI patients (FIG. 1). If the group of patients with MM is analyzed on their own a lower level of MBL was observed amongst the patients with CSI (FIG. 2).

Discussion

So far studies on the correlation between MBL deficiency and frequency of infection has been conducted by defining an arbitrary level for deficiency (e.g. 50 ng/ml[18]) or using the presence of allelic mutations of MBL on both chromosomes as indicative for deficiency[11, 12]. In the present study the patients themselves define the level were clinically symptoms becomes apparent as being below 500 ng MBL per ml. In other patients groups the level may well prove to be different as the different immunological parameters will be of varying importance in different patient populations.

The results shown in FIGS. 1 and 2 illustrate that patients with an MBL plasma concentration under 500 ng/ml is much more susceptible to infections following chemotherapy treatment. This group of patients should be offered substitution therapy with MBL during their chemotherapeutic treatments. This treatment may be initiated before the start of chemotherapy treatment and be maintained until the other immunological parameters have normalized. The MBL could be prepared from human plasma or could be produced by recombinant technology.

Evidently, one will predict that patients with other cancer forms undergoing cell toxic treatment (chemotherapy or x-ray therapy) should also benefit from treatment with MBL.

Unpublished results have shown decrease in MBL concentrations following septicaemia and treatment with MBL may thus prove a useful modality in patients first presenting normal levels of MBL.

The duration of survival of patients with MM ranges from a few months to many years. Considerable efforts have been put into attempts to define prognostic parameters for survival of cancer patients undergoing chemotherapy.

The results presented show that the concentration of MBL is a superior predictor of sepsis after chemotherapy. Measuring the concentration of MBL is thus an important prognostic parameter in patients undergoing chemotherapy and must be supposed to be likewise in patients designated for other therapeutic cell toxic treatments. Since the genotypes of the MBL gene determines the plasma concentration of MBL an analysis of the genes of MBL in an individual can indirectly be used for estimating the MBL concentration.

In the literature two studies have included measurements of MBL in cancer patients. Aittoniemi et al. analyzed patients with chronic lymphocytic leukemia (CLL) for an association between MBL deficiency and infections[25]. Only six out of 28 patients received chemotherapy,with chlorambucil-[prednisolone] in three patients, with chlorambucil-[prednisolone] and cyclophosphamide-(hydroxydaunorubicin)-oncovine-prednisolone in three patients. MBL deficiency was defined as an MBL concentration below the detection limit (<20 ng/ml) of the MBL assay used. Out of the 28 patients only one were included in the group of MBL deficient.

No attempts were made to analyze for an association between MBL levels and infection rate in the patients who had received chemotherapy. Thus, no conclusions regarding the claims of the present patent application can be drawn from that study.

Lehrnbecher et al. examined if the level of interleukin-6, interleukin-8, C-reactive protein, soluble Fc gamma receptor type III, or MBL could be an indicator of serious infections in febrile children with cancer and neutropenia[26]. A total of 56 children with a confirmed malignancy and chemotherapy-induced neutropenia were studied. The levels of MBL measured were actually not presented in the paper. It is only indicated in the text that "the level of MBL were not useful for discrimination between life-threatening infections and febrile episodes without identifiable source or probable catheter-associated bacteriaemias".

The study group in this study is different from the one presented in the present patent application as they were all children and 27 of the children was included due to a solid tumor and not because of leukemia. The remaining 29 leukemia patients are not analyzed by themselves. Without the actual data it is not possible to compare this study with the results presented here.

Other biologic and immunomodulating agents have been used in treatment of patients with neutropenia and fever. Intravenous immunoglobulin has no benefit in preventing fever or infection in patients with neutropenial but may have a moderate effect in patients with antibody deficiencies. Interferon gamma may add a benefit to patients with some neutrophil deficiencies, but this is not finally proven. Cellular growth factors (granulocyte and granulocyte-macrophage colony-stimulating factor) may shorten the duration of neutropenia and thus the need for antibiotics.

References
1. Weis W I, Taylor M E and Drickamer K (1998) The C-type lectin superfamily in the immune system. *Immunological Reviews* 163: 19–34
2. Holmskov, U., Malhotra, R., Sim, R. B., and Jensenius, J. C. (1994) Collectins: collagenous C-type lectins of the innate immune defense system. *Immunol. Today* 15:67–74.
3. Turner, M. W. (1996) Mannose-binding lectin: the pluripotent molecule of the innate immune system. *Immunol. Today* 17:532–540.
4 Janeway C A, Travers P, Walport M and Capra J D (1999) Immunobiology, the immune system in health and disease, Fourth Edition, Churchill Livingstone)
5. Matsushita, M. and Fujita, T (1992). Activation of the classical complement pathway by mannose-binding protein in association with a novel C1s-like serine protease. *J. Exp. Med.* 176:1497–1502.
6. Thiel S, Vorup-Jensen T, Stover C M, Schwaeble W, Laursen S B, Poulsen K, Willis A C, Eggleton P, Hansen S, Holmskov U, Reid K B and Jensenius J C (1997) A second serine protease associated with mannan-binding lectin that activates complement. *Nature,* 386(6624): 506–510
7. Stover C M, Thiel S, Thelen M, Lynch N J, Vorup-Jensen T, Jensenius J C and Schwaeble W J (1999) Two constituents of the initiation complex of the mannan-binding lectin activation pathway of complement are encoded by a single structure gene. *J Immunol* 162: 3481–3490
8. Thiel S, Holmskov U, Hviid L, Laursen S B and Jensenius J C (1992) The concentration of the C-type lectin, mannan-binding protein, in human plasma increases during an acute phase response. *Clin Exp Immunol* 90: 31–35
9. Madsen, H. O., Garred, P., Kurtzhals, J. A., Lamm, L. U., Ryder, L. P., Thiel, S., and Svejgaard, A. (1994) A new frequent allele is the missing link in the structural polymorphism of the human mannan-binding protein. *Immunogenetics* 40:37–44.
10. Summerfield J A, Ryder S, Sumiya M, Thursz M, Gorchein A, Monteil M A and Turner M W (1995) Mannose binding protein gene mutations associated with unusual and severe infections in adults. *Lancet* 345: 886–889
11. Garred P, Madsen H O, Hofmann B and Svejgaard A (1995) Increased frequency of homozygosity of abnormal mannan binding protein alleles in patients with suspected immunodeficiency. *Lancet* 346: 941–943
12. Summerfield J A, Sumiya M, Levin M and Turner M W (1997) Association of mutations in mannose-binding protein gene with childhood infection in consecutive hospital series. *BioMed J* 314: 1229–1232
13. van Emmerik, L C, Kuijper, E J, Fijen, CAP, Dankert, J, and Thiel, S (1994) Binding of mannan-binding protein to various bacterial pathogens of meningitis. *Clin.Exp.Immunol.* 97:411–416.
14. Jack D L, Dodds A W, Anwar N, Ison C A, Law A, Frosch M, Turner M W and Klein N J (1998) Activation of complement by Mannose-binding lectin on isogenic mutants of Neisseria meningitidis seroproup B. *J Immunol* 160: 1346–1353
15. Miller, M. E., Seals, J., Kaye, R., and Levitsky, L. C. (1968) A familial, plasma-associated defect of phagocytosis. A new case of recurrent bacterial infections. *The.Lancet* :60–63.
16. Super, M., Thiel, S., Lu, J., Levinsky, R. J., and Turner, M. W. (1989) Association of low levels of mannan-binding protein with a common defect of opsonisation. *Lancet* 2:1236–1239.
17. Nielsen, S. L., Andersen, P. L., Koch, C., Jensenius, J. C., and Thiel, S. (1995) The level of the serum opsonin, mannan-binding protein in HIV-1 antibody-positive patients. *Clin. Exp. Immunol.* 100:219–222.
18. Christiansen, O. B., Kilpatrick, D. C., Souter, V., Varming, K., Thiel, S., Jensenius,J. C. (1999) Mannan-binding lectin deficiency is associated with unexplained recurrent miscarriage. Scand. J. Immunol., 49, 193–196
19. Garred, P, Harboe, M, Oettinger, T, Koch, C, and Svejgaard, A (1994) Dual role of mannanbinding protein in infections: Another case of heterosis?*Eur.J.Immunogen.* 21:125–131.
20. Hoal-Van Helden E G, Epstein J, Victor T C, Hon D, Lewis L A, Beyers N, Zurakowski D, Ezekowitz A B, Van Helden P D (1999) Mannose-binding protein B allele confers protection against tuberculous meningitis. *Pediatr Res* 45:459–64
21. Fischer, P B, Ellerman-Eriksen, S, Thiel, S, Jensenius, J C, and Mogensen, S C (1994) Mannan-binding protein and conglutinin mediate enhancement of herpes simplex virus type-2 infection in mice. *Scand J Immunol* 39:439–445.
22. Valdimarsson H, Stefansson M, Vikingsdottir T, Arason G J, Koch C, Thiel S and Jensenius J C (1998) Reconstitution of opsonizing activity by infusion of mannan-binding lectin (MBL) to
24. Pizzo, P A (1993), Management of fever in patients with cancer and treatment-induced neutropenia, N Eng J Med, 328, 1323–1332.
25. Aittoniemi, J., Miettinen, A., Laine, S., Sinisalo, M., Laippala, P., Vilpo, L, Vilpo, J. (1999), Opsonising immunoglobulins and mannan-binding lectin in chronic lymphocytic leukemia, Leuk Lymphoma July;34(34):3815
26. Lehrnbecher T, Venzon D, de Haas M, Chanock S J, Kuhl J. (1999) Assessment of measuring circulating levels of interleukin6, interleukin8, Creactive protein, soluble Fc gamma receptor type III, and mannosebinding protein in febrile children with cancer and neutropenia. Clin Infect Dis, August;29(2):4149.
27. Lu, J., Thiel, S., Wiedemann, H., Timpl, R. & K. B. M. Reid (1990) Binding of the pentamer/hexamer forms of mannan-binding protein to zymosan activates the proenzyme $C1r_2C1s_2$ complex, of the classical pathway of complement without involvement of C1q. *J. Immunol.* 144:2287–2294.
28. Sastry, K., Herman, G. A., Day, L., Deignan, E., Bruns, G., Morton, C. C. & R. A. B. Ezekowitz (1989) The human mannose-binding protein gene. *J. Exp. Med.* 170: 1175–1189.
29. Lipscombe, R. J., Sumiya, M., Summerfield, J. A. & M. W. Turner (1995) Distinct physicochemical characteristics of human mannose-binding protein expressed by individuals of differing genotype. *Immunology* 85:660–667.

The invention claimed is:

1. A method of reducing the risk of contracting infection in an individual who is at least one of the following:
   a) an individual having an immunocompromised condition; or
   b) an individual being at risk of acquiring an immunocompromised condition resulting from a medical treatment; or
   c) an individual having a serum level of mannan-binding in excess of 50 ng/ml,
said individual having a serum level of MBL which is less than 500 ng/ml, by administering to said individual a prophylactically effective amount of a medicament composition comprising at least one MBL subunit, or at least one MDL oligomer comprising the at least one MDL subunit, whereby the risk of contracting infection in said individual is reduced.

2. The method of claim 1, wherein the composition comprises at least one mannan-binding lectin (MBL) oligomer comprising the at least one mannan-binding lectin (MBL) subunit.

3. The method of claim 2, wherein said oligomer is preferably selected from the group of oligomers consisting of tetramers, pentamers and hexamers.

4. The method of claim 1, wherein the individual, having an immunocompromised condition, has a serum level of MBL in excess of 50 ng/ml.

5. The method of claim 1, wherein the individual, being at risk of acquiring an immunocompromised condition resulting from a medical treatment, has a serum level of MBL in excess of 50 ng/ml.

6. The method of claim 1, wherein the serum MBL level is the functional serum MBL level.

7. The method of claim 1, wherein said immunocompromised condition is neutropenia.

8. The method of claim 1, wherein said immunocompromised condition is autoimmune neutropenia.

9. The method of claim 1, wherein the infection is an infection caused by a microbial species.

10. The method of claim 9, wherein the microbial species is a fungus.

11. The method of claim 9, wherein the microbial species is a yeast.

12. The method of claim 9, wherein the microbial species is a bacteria.

13. The method of claim 12, wherein the bacterial species is resistant to at least one antibiotic medicament.

14. The method of claim 12, wherein the bacterial species is multiresistant.

15. The method of claim 12, wherein the bacterial species is pathogenic.

16. The method of claim 9, wherein the infection is a viral infection.

17. The method of claim 16, wherein the virus is a retrovirus.

18. The method of claim 17, wherein the retrovirus is a Human Immunodeficiency Virus.

19. The method of claim 1, wherein the MBL subunit or the MBL oligomer is produced in a native host organism.

20. The method of claim 19, wherein the native host organism is a human cell natively expressing the MBL subunit or the MBL oligomer.

21. The method of claim 19, wherein the MBL subunit or the MBL oligomer is isolated from the host organism.

22. The method of claim 21, wherein the MBL subunit or the MBL oligomer is isolated by a method comprising at least one step involving affinity chromatography.

23. The method of claim 1, wherein the MBL subunit or MBL oligomer is produced by a host organism not natively expressing an MBL polypeptide.

24. The method of claim 23, wherein the production of the MBL subunit or the MBL oligomer is controlled by an expression control sequence not natively associated with MBL polypeptide expression.

25. The method of claim 23, wherein the MBL subunit or the MBL oligomer is isolated from the host organism.

26. The method of claim 25, wherein the MBL subunit or the MBL oligomer is isolated by a method comprising at least one step involving affinity chromatography.

27. The method of claim 26, wherein the affinity chromatography step isolates MBL tetramers, pentamers, hexamers or the combination thereof from a composition further comprising additional MBL oligomers, MBL subunits, or both.

28. The method of claim 1, wherein the MBL subunit or the MBL oligomer is produced by a method comprising at least one step of recombinant DNA technology in vitro.

29. The method of claim 28 wherein the production of the MBL subunit or the MBL oligomer is controlled by an expression control sequence not natively associated with MBL polypeptide expression.

30. The method of claim 1, wherein the MBL subunit, the MBL oligomer, or the combination thereof is free from any impurities naturally associated with the MBL when produced in a native host organism.

31. The method of claim 1, wherein the MBL subunit is a mammalian MBL subunit.

32. The method of claim 31, wherein the mammalian MBL subunit is a human MBL subunit.

33. The method of claim 1, wherein the medicament is administered to the individual prior to, during, or after a medical treatment resulting in an immunocompromising condition in the individual.

34. The method of claim 33, wherein the medicament is administered to the individual prior to said medical treatment.

35. The method of claim 33, wherein said medical treatment is chemotherapy.

36. The method of claim 33, wherein said medical treatment is radiation therapy.

37. The method of claim 1, wherein the medicament is a booster of MBL serum levels in an individual having MBL serum levels above a predetermined minimum MBL serum level of 50 ng/ml.

38. The method of claim 1, wherein the individual has serum levels of MBL in excess of 75 ng/ml.

39. The method of claim 1, wherein the individual has serum levels of MBL below 400 ng/ml.

40. The method of claim 1, wherein serum or plasma levels of MBL in the individual are determined by quantitative analysis.

41. The method of claim 40, wherein the analysis comprises at least one of enzyme linked immunosorbent assay (ELISA), time-resolved immunofluorescent assay (TRIFMA), radioimmunoassay (RIA) or nephelometry.

42. The method of claim 1, said composition further comprising an additional antimicrobial medicament effective against said infection.

43. The method of claim 1, where, prior to administering said composition, the serum level of MBL in said individual was measured, and said serum level was found to be in excess of 50 ng/ml serum.

* * * * *

UNITED STATES PATENT AND TRADEMARK OFFICE
CERTIFICATE OF CORRECTION

PATENT NO. : 7,202,207 B2 Page 1 of 1
APPLICATION NO. : 10/424769
DATED : April 10, 2007
INVENTOR(S) : Thiel et al.

It is certified that error appears in the above-identified patent and that said Letters Patent is hereby corrected as shown below:

Column 15, line 10 (claim 1), before the word "in" insert --lectin (MBL) --.
Column 15, claim 1, both instances of "MDL" should read --MBL--.

Signed and Sealed this

Thirteenth Day of November, 2007

JON W. DUDAS
*Director of the United States Patent and Trademark Office*